United States Patent
Ozcan et al.

(10) Patent No.: US 8,842,901 B2
(45) Date of Patent: Sep. 23, 2014

(54) COMPACT AUTOMATED SEMEN ANALYSIS PLATFORM USING LENS-FREE ON-CHIP MICROSCOPY

(75) Inventors: Aydogan Ozcan, Los Angeles, CA (US); Anthony F. Erlinger, New York, NY (US); Ting-Wei Su, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 261 days.

(21) Appl. No.: 13/324,941

(22) Filed: Dec. 13, 2011

(65) Prior Publication Data
US 2012/0148141 A1 Jun. 14, 2012

Related U.S. Application Data (60) Provisional application No. 61/423,049, filed on Dec. 14, 2010.

(51) Int. Cl.
| | | |
|---|---|---|
| *G06K 9/00* | (2006.01) | |
| *G06T 7/00* | (2006.01) | |
| *G03H 1/04* | (2006.01) | |

(52) U.S. Cl.
CPC .......... *G06K 9/00127* (2013.01); *G06K 9/0014* (2013.01); *G06T 2207/10056* (2013.01); *G06T 7/0012* (2013.01); *G03H 2001/0447* (2013.01); *G06T 2207/10016* (2013.01); *G06T 2207/30242* (2013.01); *G03H 1/0443* (2013.01)
USPC .......................................... 382/133; 382/103

(58) Field of Classification Search
None
See application file for complete search history.

(56) References Cited

U.S. PATENT DOCUMENTS

| | | | |
|---|---|---|---|
| 4,896,967 A * | 1/1990 | Douglas-Hamilton et al. ............................. | 382/128 |
| 5,895,749 A | 4/1999 | Alvarez | |
| 5,935,800 A | 8/1999 | Alvarez | |
| 6,011,015 A * | 1/2000 | Vinson ........................... | 514/9.8 |
| 6,426,213 B1 * | 7/2002 | Eisenson ................... | 435/288.7 |

OTHER PUBLICATIONS

Budkeyich et al. "Amplitude-Phase Hologram recording", Translated from Zhurnal Prikladnoi Spektroskopii, vol. 50, No. 6, pp. 621-624, Jun. 1989.*
Segerink, L. I. et al., On-chip determination of spermatozoa concentration using electrical impedance measurements, Lab Chip 2010, 10, 1018-1024.
Seo, S. et al, Lensfree holographic imaging for on-chip cytometry and diagnostics, Lab Chip 2009, 9, 777-787.
Su, T. et al., Multi-angle lensless digital holography for depth resolved imaging on a chip, Opt. Express 2010, 18, 9690-9711.

(Continued)

*Primary Examiner* — Randolph I Chu
(74) *Attorney, Agent, or Firm* — Vista IP Law Group LLP (57) ABSTRACT

A compact and light-weight lens-free platform to conduct automated semen analysis is disclosed. The device employs holographic on-chip imaging and does not require any lenses, lasers or other bulky optical components to achieve phase and amplitude imaging of sperm a relatively large field-of-view with an effective numerical aperture of approximately 0.2. A series of digital image frames is obtained of the sample. Digital subtraction of the consecutive lens-free frames, followed by processing of the reconstructed phase images, enables automated quantification of the count, the speed and the dynamic trajectories of motile sperm, while summation of the same frames permits counting of immotile sperm.

20 Claims, 8 Drawing Sheets

(56) References Cited

OTHER PUBLICATIONS

Su et al., Compact and Light-Weight Automated Semen Analysis Platform Using Lensfree on-Chip Microscopy, Anal Chem. Oct. 1, 2010; 82(19): 8307-8312.

Hardie et al., Joint MAP Registration and High-Resolution Image Estimation Using a Sequence of Undersampled Images, IEEE, vol. 6 No. 12, Dec. 1997.

Ozcan et al., Ultra wide-filed lens-free monitoring of cells on-chip, Lab on Chip 8, 89-106, Nov. 1, 2007.

Ozcan et al., Lens-free On-Chip Cytometry for wireless Health Diagnosis, IEEE LEOS Newsletter, Oct. 2008.

Seo et al., Lensfree On-chip Cytometry Using Tunable Monochromatic Illumination and Digital Noise Reduction, Multi-color LUCAS, Sep. 2008.

Su et al., Towards Wireless Health: Lensless On-Chip Cytometry, Biophotonics, Dec. 2008.

Su et al., High-Throughput Lensfree Imaging and Characterization of Heterogeneous Cell Solution On a Chip, Biotechnology and Bioengineering, Sep. 8, 2008.

Isikman et al., Lensfree Cell Holography on a Chip: From Holographic Cell Signatures to Microscopic Reconstruction, LEOS Annual Meeting Conf. Proceedings, Oct. 2009.

Mudanyali et al., Lensless On-chip Imaging of Cells Provides a New Tool for High-throughput Cell-Biology and Medical Diagostics, Journal of Visualized Experiments, Dec. 14, 2009.

Bishara et al., Lensfree on-chip microscopy over a wide field-of-view using pixel super-resolution, Optics Express, vol. 18 No. 11, May 24, 2010.

Coskun et al., Wide field-of-view lens-free fluorescent imaging on a chip, Lab Chip, 10(7), 824-827, Apr. 7, 2010.

Coskun et al., Lensless wide-field fluorescent imaging on a chip using compressive decoding of sparse objects, Optics Express, vol. 18 No. 10, May 5, 2010.

Khademhosseinieh et al., Lensfree color imaging on a nanostructured chip using compressive decoding, Applied Physics Letters, 97, 211112-1, Nov. 24, 2010.

Khademhosseinieh et al., Lensfree on-chip imaging using nanostructured surfaces, Applied Physics Letters, 96, 171106, Apr. 30, 2010.

Mudanyali et al., Compact, light-weight and cost-effective microscope based on lensless incoherent holography for telemedicine applications, Lab Chip, 10, 1417-1428, Apr. 19, 2010.

Ozcan, Smart technology for global access to healthcare, SPIE, Mar. 16, 2010.

Ozcan et al., Lensfree on-chip holography facilitates novel microscopy applications, SPIE, May 19, 2010.

\* cited by examiner

COMPACT AUTOMATED SEMEN ANALYSIS PLATFORM USING LENS-FREE ON-CHIP MICROSCOPY

RELATED APPLICATION

This Application claims priority to U.S. Provisional Patent Application No. 61/423,049 filed on Dec. 14, 2010. Priority is claimed pursuant to 35 U.S.C. §119. The above-noted Patent Application is incorporated by reference as if set forth fully herein.

FIELD OF THE INVENTION

The field of the invention generally relates to methods and devices for imaging of microscopic structures such as cells and particles. More particularly, the field of the invention pertains to systems and methods for the imaging of cells or particles flowing within a microfluidic environment.

BACKGROUND

Semen analysis is an important routine that is extensively practiced in laboratories for evaluating male fertility and preparing artificial insemination. To determine the sperm concentration in semen, the current "gold standard" requires a visual assessment of a sperm sample placed into a counting chamber. The sperm are then manually counted through an optical microscope. Not only that this method is recommended by the World Health Organization (WHO), but also it is widely used in most laboratories that process semen. Due to the labor intensive nature of this manual method, several other optical approaches, including turbidimetry, laser Doppler velocimetry (LDV), and photon correlation spectroscopy have also been proposed to automatically analyze semen. However, these approaches are still not widely adopted partially because they can only provide indirect estimations of the sperm concentration and motility.

Currently, Computer-Assisted Semen Analysis (CASA) systems, which utilize pattern analysis algorithms to automatically process the optical images recorded with a conventional optical microscope, is considered as one of the most promising technologies to replace the traditional manual semen analysis method. An important feature of CASA systems is their ability to provide quantitative information about sperm motility, such as the speed distribution of individual sperm cells, which has been proven to be rather important for predicting fertilization rate as well as for evaluation of the correlation between various drugs and sperm quality. However, despite the fact that state-of-the-art CASA systems are very efficient and versatile, their relatively large dimensions, high cost and maintenance needs partially hinder their widespread use in fertility clinics. For the same reason, application of this platform to field-use in veterinary medicine such as stud farming and animal breeding has also been significantly limited.

In addition to these, commercially available male fertility test kits for personal home use, such as FertilMARQ (U.S. Pat. Nos. 5,895,749 and 5,935,800) or SpermCheck, also aim to indirectly quantify sperm concentration by a color change due to chemical staining or labeling of sperm-specific proteins. These tests, however, cannot quantify sperm motility or the concentration of motile sperm. Recently, an alternative semen analysis platform involving a compact micro-fluidic device that can measure electrical impedance changes due to sperm movement has also been reported. See Segerink, L. I. et al., On-chip determination of spermatozoa concentration using electrical impedance measurements, Lab Chip 2010, 10, 1018-1024. However, this lab-on-a-chip platform can only provide the total number of the sperm in the sample and cannot differentiate motile and immotile sperm from each other, which is an important limitation.

SUMMARY

In one embodiment, a compact imaging platform is described that semen analysis using lens-free optical components. The imaging platform relies on partially coherent digital in-line holography to create on-chip images of spermatozoa. In this approach, a partially coherent visible light source (quasi-monochromatic with a spectral bandwidth of e.g., ~5 nm) illuminates a sample containing sperm. Within a few centimeters of free-space propagation, the illumination light picks up partial spatial coherence, the extent of which is sufficient to record lens-free in-line holograms of the sperm.

The lens-free holograms of the sperm are then digitally sampled by the image sensor (e.g., a CMOS chip). The light source, image sensor, sample holder, all without any lenses or mechanical components are contained in a compact device measuring approximately 4.2×4.2×5.8 cm and weighing approximately 46 grams. The device provides an imaging field-of-view (FOV) of around 24 mm$^2$ together with a numerical aperture (NA) of approximately 0.2.

This imaging FOV is more than 20 fold larger than the FOV of a typical 10× objective-lens, and therefore provides a significant throughput advancement that permits automated monitoring of hundreds to thousands of sperm all in parallel. This lens-free on-chip imaging device is, as noted above, based on digital in-line holography, and it utilizes an incoherent or partially coherent light source such as a light emitting diode (LED) that is filtered by a large aperture of ~0.1 mm to illuminate the sample of interest.

Over a short propagation distance of ~4 cm, this illumination light picks up partial spatial coherence, after which it scatters from each sperm to coherently interfere with the background light, forming lens-free holograms of the sperm over a large FOV (~24 mm$^2$). These lens-free sperm holograms can then be rapidly processed (e.g., <1 sec) using a Graphics Processing Unit (GPU) to reconstruct their microscopic images (both amplitude and phase).

To conduct automated semen analysis using this lens-free holographic device about twenty (20) holographic frames are captured over approximately ten (10) seconds. Digital summation of all these lens-free frames removes the moving sperm out of the picture and enables one to rapidly count only the immobile sperm based on the reconstructed phase images. On the other hand, digital subtraction of these consecutive holographic frames from each other removes the immobile sperm out of the picture, leaving behind only the moving or motile ones, which permits automatic quantification of the individual speed and the trajectories of all the motile sperm within an FOV of ~24 mm$^2$. The performance of this platform for automated semen analysis has been verified by comparing the obtained results against manual analysis of the same samples conducted using a conventional bright-field microscope. The compact, light-weight and cost-effective automated semen analysis platform running on a wide-field lens-free on-chip device would be especially useful for fertility clinics, personal male fertility tests, as well as for field-use in veterinary medicine.

In one embodiment, a system for the automated analysis of sperm includes an imager comprising a sample holder configured to receive a sample containing sperm and an illumination source configured to illuminate a first side of the sample holder through a spatial filter interposed between the illumination source and the sample holder. The system includes an image sensor disposed on a second, opposite side of the sample holder configured to acquire at least one image frame of the sperm in the sample. A processing unit is configured to receive the at least one image frame from the image sensor, the processing unit configured identify and count sperm in the at least one image frame.

In another embodiment, a method of automatically analyzing immotile sperm includes illuminating a first side of a sample holder configured to receive a sample containing sperm with an illumination source emitting at least partially coherent light, the at least partially coherent light passing through an aperture prior to illuminating the sample holder. A plurality of image frames of the sample are acquired with an image sensor disposed on an opposing side of the sample holder. A summation hologram is created based on a digital summation of the plurality of image frames. The summation hologram is reconstructed into frame images containing amplitude and phase information. The sperm heads in the reconstructed phase image are isolated and the orientation of each sperm head is identified. Sperm tails having a tail length above a threshold value and a tail orientation aligned with the orientation of each sperm head are identified. The number of immotile sperm are counted based on the total number of sperm having a tail length above a threshold value and a tail orientation aligned with the orientation of each sperm head.

In another embodiment, a method of automatically analyzing motile sperm includes illuminating a first side of a sample holder configured to receive a sample containing sperm with an illumination source emitting at least partially coherent light, the at least partially coherent light passing through an aperture prior to illuminating the sample holder. A plurality of image frames of the sample are acquired with an image sensor disposed on an opposing side of the sample holder. Consecutive image frames are digitally subtracted and produce an image representative of motion of the sperm. Motile sperm are identified in the image representative of motion of the sperm and the number of mobile sperm are counted.

DETAILED DESCRIPTION OF THE ILLUSTRATED EMBODIMENTS

Figure 1:
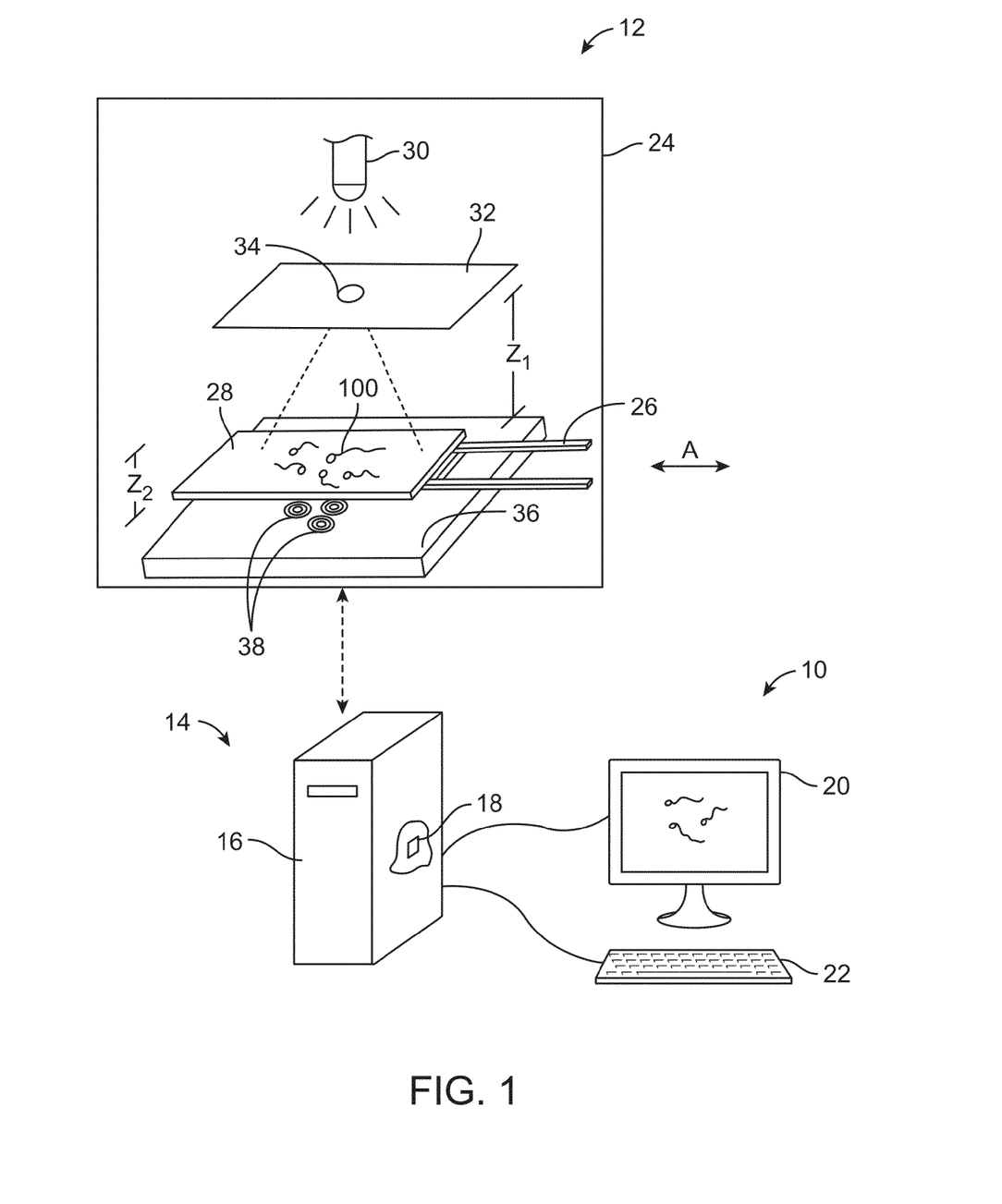
FIG. 1 illustrates a schematic of a system for the automated analysis (e.g., counting) of sperm according to one embodiment.

FIG. 1 schematically illustrates a system 10 for the automated image analysis of sperm cells 100. The system 10 includes an imager 12 that is small and compact that functions as the microscope aspect of the system 10 though there are no lenses or other moving components typically found in larger and more expensive optical microscopes. The system 10 also includes a processing unit 14 in which image analysis is performed. The processing unit 14 may be a computer 16 such as that illustrated in FIG. 1. Alternatively, the processing unit 14 may include one or more dedicated processors. For example, the processing unit 14 may include a Graphics Processing Unit (GPU). As seen in FIG. 1, the computer 16 contains therein at least one processor 18 that may be used to perform the image processing routines described herein. While the imager 12 and the processing unit 14 are illustrated in FIG. 1 as physically separate it should be understood that it may be possible to incorporate the processing unit 14 into the imager 12. For example, as electronics components get smaller and more powerful, it may be possible to integrate the processing unit 14 into the imager 12. The imager 12 may even utilize the processing capability of a wireless or other mobile device (not shown).

As seen in FIG. 1, the computer 16 may be connected to a display 20 as well as one or more input devices 22 such as a keyboard, mouse, or the like. Images or other information regarding the analysis such as sperm count, sperm motility (e.g., displacement, mean speed, average speed) may be viewed on the display 20. The user may interface with the computer 16 via the input device 22. For example, the user may select what images are to be viewed on the display 20. Alternatively, the user may select the particular functionality that is to be displayed on the display 20 such as total number of immotile sperm, total number of motile sperm, sperm trajectories, sperm speed, sperm rejection rates, etc.

Still referring to FIG. 1, the imager 12 is contained within a housing 24 that contains therein all the components imaging components therein. The housing 24 may be made of a robust material such as plastic or metal. Preferably, the housing 24 is compact and generally is hand-held. Located inside the housing is sample tray 26 that is configured to hold a sample holder 28. The sample tray 26 is preferably movable as illustrated by arrow A in FIG. 1 such that the sample holder 28 can be loaded into the sample tray 26 from outside the housing 24 and then inserted into the housing 24 such that the sample holder 28 is disposed in the optical path as described herein. The sample holder 28 may include an optically transparent substrate such as glass, plastic, or the like on or in which a sample is placed. For example, a microscope glass cover slip may be used as the sample holder 28. The sample holder 28 may include a multilayer substrate in which the sample is sandwiched there between or the sample may simply be loaded onto the top of a substrate.

The sample can be loaded on or in the sample holder 28 in any conventional fashion using pipette, capillary, or other commonly used transfer means. The sample may include mammalian ejaculate that contains sperm cells 100 therein. The sperm sample may need some pre-processing (e.g., washing, dilution) prior to loading on the sample holder 28. FIG. 1 illustrates sperm cells 100 loaded onto the sample holder 28.

Still referring to FIG. 1, the imager 12 includes an illumination source 30 that is configured to illuminate a first side (top side as seen in FIG. 1) of the sample holder 28. The illumination source 30 is preferably a spatially incoherent or a partially coherent light source. Light emitting diodes (LEDs) are one example of an illumination source 30. LEDs are relative inexpensive, durable, and have generally low power requirements. Of course, other light sources may also be used such as a Xenon lamp with a filter. As seen in FIG. 1, a spatial filter 32 is interposed between the illumination source 30 and the sample holder 28. The spatial filter 32 has an aperture 34 contained therein that is configured to permit the passage of illumination. The aperture 34 has a diameter (D) that is typically in the range of 50 µm to about 100 µm.

As seen in FIG. 1, an image sensor 36 is disposed on a second, opposite side of the sample holder 28 such that the sample holder 28 is interposed between the illumination source 30 and the image sensor 36. The image sensor 36 is located adjacent to the back side of the sample holder 28. The surface of image sensor 36 may be in contact with or close proximity to the back side of the sample holder 28. For example, the sample holder 28 may be placed directly atop the glass or other optically transparent layer that typically covers the image sensor 36. The image sensor 36 may include, for example, a charged coupled device (CCD) or a complementary metal-oxide semiconductor (CMOS) device. The image sensor 36 may be monochromatic or color. The image sensor 36 generally has a small pixel size which is less than 9.0 µm in size and more particularly, smaller than 5.0 µm in size (e.g., 2.2 µm or smaller). Generally, image sensors 36 having smaller pixel size will produce higher resolutions.

Still referring to FIG. 1, the spatial filter 32 is located at a distance $z_1$ from the sample holder 28. The imaging plane of the image sensor 36 is located at a distance $z_2$ from the sample holder 28. In the system 10 described herein, $z_2 \ll z_1$. For example, the distance $z_1$ may be on the order of around 1 cm to around 10 cm. In other embodiments, the range may be smaller, for example, between around 5 cm to around 10 cm. The distance $z_2$ may be on the order of around 0.05 mm to 2 cm, however, in other embodiments this distance $z_2$ may be between around 1 mm to 2 mm. In the system 10, the propagation distance $z_1$ is such that it allows for spatial coherence to develop at the plane of the sperm cells 100, and light scattered by the sperm cells 100 interferes with background light to form a lens-free in-line holograms 38 on the image sensor 36.

Still referring to FIG. 1, the system 10 includes a computer 16 such as a laptop, desktop, or the like that is operatively connected to the image sensor 36 such that holographic images are transferred from the image sensor 36 to the computer 16 for data acquisition and image processing. The computer 16 includes one or more processors 18 that, as described herein in more detail, runs or executes software that acquires holographic images of the sperm cells 100. The software on the computer 16 can perform digital subtraction of consecutively taken lens-free images, followed by processing of the reconstructed lost phase of the images to enable automated quantification of the count, speed, and dynamic trajectories of the motile sperm cells 100. Conversely, the same software can be used to perform digital summation of the image frames to count the immotile sperm cells 100.

Figure 2:
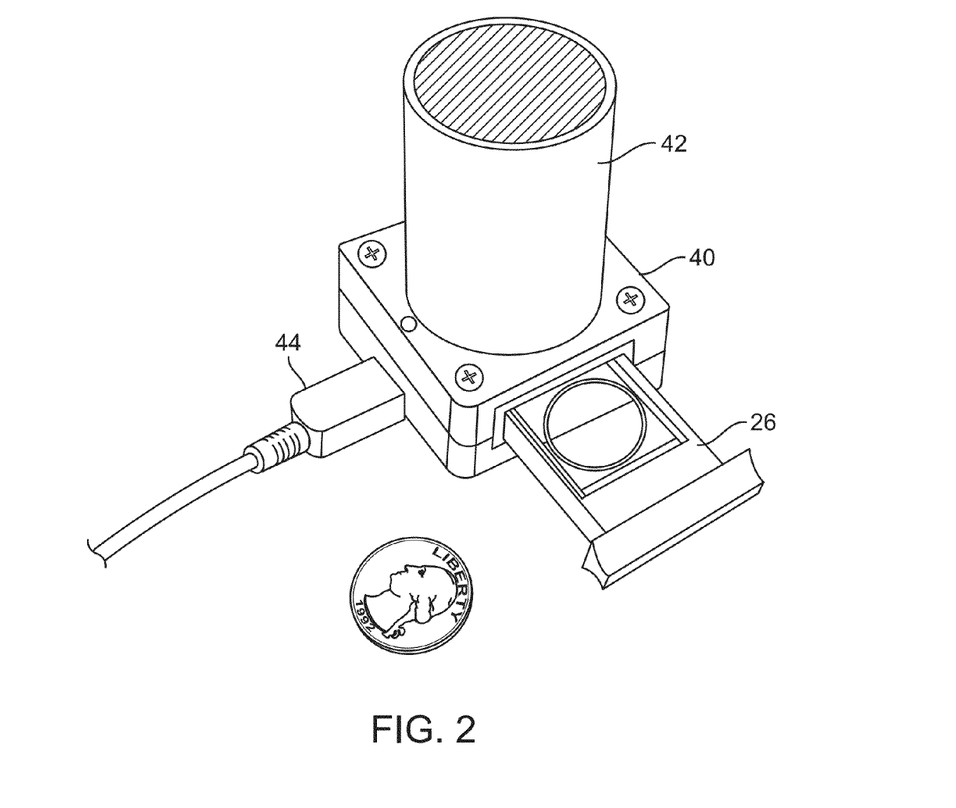
FIG. 2 is an image of one embodiment of a system for the automated analysis of sperm.

The imager 12 in FIG. 1 may be powered by an internal power source (not shown) such as a battery or the like. The battery powers both the illumination source 30 as well as the image sensor 36. Alternatively, as illustrated in FIG. 2, the imager 12 may be powered by an external power source. For example, a USB cable may interface with the imager 12 which acts both to deliver power to the imager 12 as well as transfer date from the image sensor 36 to the computer 16 or external processing unit 14.

FIG. 2 illustrates a perspective view of an imager 12 according to one embodiment. The imager 12 includes a housing 24 which may be formed from multiple sub-assemblies. For instance, the imager 12 of FIG. 12 includes a generally square-shaped base portion 40 along with a cylindrically-shaped extended portion 42. The particular geometrical profile of portions 40, 42 is immaterial. The base portion 40 generally houses the sample tray 26 which is illustrated in FIG. 2 in an extended state. The base portion 40 also includes the image sensor 36 (not shown in FIG. 2). The extended portion 42 contains the illumination source 32 and spatial filter 32 (both not seen due to housing 24). A cable 44 is shown connecting to the imager 12. The cable 44 may include functionality for providing power and/or data transfer to and from the imager 12 to a processing unit 14 or computer 16. For example, the cable 44 illustrated in FIG. 2 is a standard USB cable that can be used for both power delivery and data transfer. A quarter is illustrated in FIG. 2 to give perspective as to the size of the imager 12. The imager 12 of FIG. 2 has dimensions of around 4.2 cm×4.2 cm×5.8 cm (height of extended portion 42). The imager 12 weighs 46 grams although the weight may vary. Nonetheless, the imager 12 is compact and portable and capable of being hand-held. The imager 12 has an effective numerical aperture (NA) of around 0.2 without using any lenses or scanning mechanical components.

Figure 3:
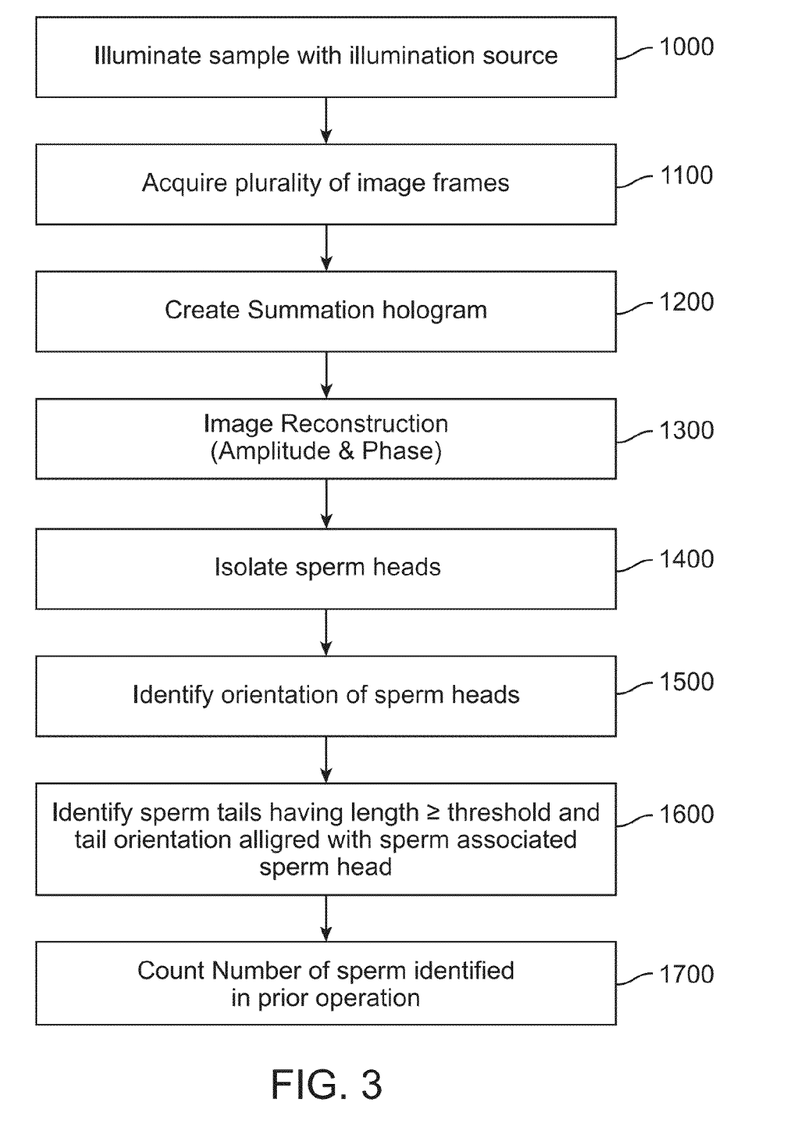
FIG. 3 illustrates a top-level flowchart of how the system automatically analyzes and counts the number of immotile sperm cells in a sample.

FIG. 3 illustrates a top-level flowchart of how the system 10 automatically analyzes and counts the number of immotile sperm cells 100 in a sample. Immotile sperm cells 100 are those sperm cells 100 that do not move. As seen in operation 1000 of FIG. 3, a sample containing sperm 100 is loaded into the imager 12 and the illumination source 30 is turned on to illuminate the sample. Raw holographic images 38 are then obtained in operation 1100 using the image sensor 36. Next, in operation 1200, the multiple image frames are digitally added or summed together to remove the moving, motile sperm 100 out of the images. This enables one to rapidly count only the remaining immotile sperm 100.

Next, in operation 1300 the amplitude and the lost phase information is then recovered from the digitally summed image. This operation is iterative holographic reconstruction algorithm that reconstructs images containing both amplitude and phase information.

For digital reconstruction of the diffraction patterns there are two approaches that can be used: (1) Back-propagate the Fourier components of the intensity of the diffraction pattern; and (2) Recover the 2D phase of the amplitude of each diffraction pattern. These two techniques independently enabled twin-image free reconstruction. These digital reconstruction approaches can actually be considered to be part of a broader umbrella of Interferometric and Non-interferometric Phase-Retrieval Techniques. In both of these approaches, the transfer function of the Rayleigh-Sommerfeld integral without any approximations has been used for back-propagating the fields.

The first approach mentioned above works with the intensity of the detected diffraction pattern, and is susceptible to the well-known twin image problem. To eliminate the twin image artifact in this first approach a numerical algorithm was implemented that can iteratively clean the reconstructed images from the twin image. In the second reconstruction method, the amplitudes of the lens-free diffraction pattern (rather than their intensities) are used to recover the 2D phase information of the complex diffraction field that was lost during the detection process. Once the entire complex diffraction field is recovered, the microscopic image can be calculated without any twin image artifact through back-propagation of the complex field.

The phase recovery approach treats the detected quantity as the amplitude of a complex diffraction field, and tries to iteratively recover its phase for digital reconstruction. Therefore the phase recovery based reconstruction approach is especially useful for where the cross-interference terms start to dominate over holographic diffraction. As a trade-off, the space-bandwidth product that is required at the detector end is increased by two fold for the phase recovery technique when compared to the first approach, since the latter one does not only deal with the holographic diffraction term, but also deals with self-interference terms.

The reconstruction process can utilize successive fast Fourier transform (FFT) operations, where after the initial FFT of each iteration, transfer function of Rayleigh-Sommerfeld integral without any approximations has been applied to the Fourier components of the diffraction pattern. Because FFT is used, the presented recoveries are also quite fast in terms of digital computation time, with a convergence time within 15 iterations taking less than 0.2 seconds using a Graphics Processing Unit (GPU).

In order to diffract the wavefronts, the angular spectrum approach is used to numerically solve the Rayleigh-Sommerfeld integral. This computation involves multiplying the Fourier transform of the field with the transfer function of propagation through linear, isotropic media, as shown below:

$$H_z(f_x, f_y) = \begin{cases} \exp\left(j2\pi z \frac{n}{\lambda}\right)\sqrt{1 - (\lambda f_x/n)^2 - (\lambda f_y/n)^2}, & \sqrt{f_x^2 + f_y^2} < \frac{n}{\lambda} \\ 0, & \text{otherwise} \end{cases} \quad (1)$$

where $f_x$ and $f_y$ are the spatial frequencies and $\eta$ is the refractive index of the medium.

Two different iterative approaches, as explained above, can be taken in order to reconstruct the image, free from any twin-image artifact. In both methods, the raw diffraction patterns are up-sampled typically by a factor of four to six, using cubic spline interpolation before the iterative reconstruction procedure. Although up-sampling does not immediately increase the information content of the diffraction patterns, it still offers significant improvements for achieving a more accurate phase recovery and higher resolution in the reconstructed image. Through the iterative reconstruction steps detailed below, these higher spatial frequencies gradually attain non-zero energy, which allows sub-pixel resolution in the final reconstruction.

Method 1: The first method falls under the broad category of Interferometric Phase-Retrieval Techniques and is applicable to cases where the recorded intensity is dominated by the holographic diffraction terms. The first step is the digital reconstruction of the hologram, which is achieved by propagating the hologram intensity by a distance of $z_2$ away from the hologram plane yielding the initial wavefront $U_{rec}$. As a result of this computation, the virtual image of the object is recovered together with its spatially overlapping defocused twin-image. It is important to note that the recorded intensity can also be propagated by a distance of $-z_2$. In this case, the real image of the object can be recovered, while the defocused virtual image leads to the twin-image formation.

In order to eliminate the twin-image artifact, an iterative approach using finite support constraints is utilized. Essentially, this technique relies on the fact that duplicate information for the phase and amplitude exists in two different reconstruction planes at distances $+z_2$ and $-z_2$ from the hologram plane, where the virtual and real images of the object are recovered, respectively. Therefore, a twin-image-free reconstruction in one of the image planes can be obtained, while filtering out the duplicate image in the other plane. Without loss of generality, the real image was filtered out to obtain a twin-image-free reconstruction in the virtual image plane at $-z_2$. The real image of the imaging plane only occupies the region inside its support, while the defocused twin-image image spreads out to a wider region around the object, also overlapping with the real image inside the support. Hence, deleting the information only inside the support ensures that the real image is completely removed from the reconstructed wavefront. Nevertheless, the virtual image information inside the support is also lost, and the iterative technique tries to recover the missing information of the virtual image by going back and forth between the virtual and real image planes, recovering more of the lost information at each iteration.

The steps of twin-image elimination are detailed below.

a) Initially the real image, which is the back-projected hologram at a distance of $+z_2$, is used for determining the object support. Object support can be defined by either thresholding the intensity of the reconstructed image, or searching for its local minima.

b) The region inside the support is deleted and a constant value is assigned to this region as an initial guess for the deleted part of the virtual image inside the support as shown below:

$$U_{z_2}^{(i)}(x, y) = \begin{cases} U_{rec}, & x, y \notin S \\ \overline{U}_{rec}, & x, y \in S \end{cases} \quad (2)$$

Where $U_z^{(i)}(x,y)$ denotes the field at the real image plane after the $i^{th}$ iteration. S represents the area defined by the object support, and $\overline{U}_{rec}$ is the mean value of $U_{rec}$ within the support.

c) Then, the field at the real image plane is back propagated by $-2z_2$ to the virtual image plane. Ideally, the reconstruction at this plane should be free from any twin-image distortions. Therefore, the region outside the support can be set to a d.c. background value to eliminate any remaining out-of-focus real image in the virtual image plane. However, this constraint is applied smoothly as determined by the relaxation parameter β below, rather than sharply setting the image to d.c. level outside the support:

$$U_{-z_2}^{(i)}(x, y) = \begin{cases} D - \dfrac{D - U_{-z_2}^{(i)}}{\beta}, & x, y \notin S \\ U_{-z_2}^{(i)}, & x, y \in S \end{cases} \quad (3)$$

where D is the background in the reconstructed field, which can either be obtained from a measured background image in the absence of the object, or can simply be chosen as the mean value of the field outside the object supports at the virtual image plane. β is a real valued parameter greater than unity, and is typically chosen around 2-3. Increasing β leads to faster convergence, but compromises the immunity of the iterative estimation accuracy to background noise.

d) The field at the virtual image plane is forward propagated to the real-image plane, where the region inside the support now has a better estimate of the missing part of the virtual image. The region outside the support can be replaced by $U_{z_2}^{(1)}(x,y)$, the original reconstructed field at the real image plane, as shown below:

$$U_{z_2}^{(i+1)}(x, y) = \begin{cases} U_{z_2}^{(1)}, & x, y \notin S \\ U_{z_2}^{(i+1)}, & x, y \in S \end{cases} \quad (4)$$

Steps c to d can be repeated iteratively until the final image converges. By replacing the intensity at the detector plane with the measured one, and keeping the updated phase distribution, one can start the next iteration to better estimate the phase of the diffracted field after each cycle. Convergence is achieved after 10-15 iterations, which takes much less than a minute on a computer with a modest hardware configuration.

Method 2: The second method utilized for eliminating the twin-image is classified under Non-Interferometric Phase-Retrieval Techniques, where the recorded image is treated as the intensity of any diffraction field. Together with the constraint that the imaging field has finite support, this technique is capable of iteratively recovering the phase of the diffracted field incident on the detector from a single intensity image. As a result, the complex field (amplitude and phase), rather than the intensity, can be back-propagated, thereby allowing reconstruction of the objects free from any twin-image contamination. This method can be decomposed into the following steps:

a) The square-root of the recorded diffraction pattern intensity is propagated by a distance of $-z_2$ to the object plane, assuming a field phase of zero as an initial guess. The aim of the algorithm is to iteratively determine the actual phase of the complex field at the image sensor plane, and eventually at the object plane. In the first iteration, the object support is defined either by thresholding the intensity of the field at the object plane, or by locating its regional maxima and/or minima.

b) The field inside the object supports is preserved, while the complex field values outside the supports is replaced by a background value $D_{-z_2}(x,y)$, as shown below:

$$U_{-z_2}^{i+1}(x, y) = \begin{cases} m \cdot D_{-z_2}(x, y), & x, y \notin S \\ U_{-z_2}^{i}(x, y), & x, y \in S \end{cases} \quad (5)$$

where $D_{-z_2}(x,y)$ is obtained by propagating the square root of the background intensity of the image obtained by the same setup in the absence of the cells; and m=mean($U_{-z_2}^{i}(x,y)$)/mean($D_{-z_2}(x,y)$).

c) The modified field at the object plane is propagated back to the detector plane, where the field now has a non-zero phase value. The amplitude of this field is replaced with the square root of the original recorded hologram intensity as no modification for the amplitude should be allowed while converging for its phase. Consequently, $U_0^{(i)}(x,y)$, the complex diffraction field at the detector plane after the $i^{th}$ iteration can be written as follows:

$$U_0^{(i)}(x,y)=|U_0^{(0)}(x,y)|\cdot\exp(\varphi_o^{(i)}(x,y)) \quad (6)$$

where the superscripts denote the iteration step, and $\varphi_o^{(i)}(x,y)$ denotes the phase of the field after the $i^{th}$ iteration.

Steps a to c can be iterated until the phase recovery converges. Typically, the results presented herein are obtained with less than fifteen (15) iterations, which is quite similar to the first Method.

Still referring to FIG. 3, after image reconstruction, the sperm heads are isolated from the reconstructed phase image as seen in operation 1400. Isolating the sperm heads occurs through a thresholding operation wherein pixels above a certain intensity value relative to the background were grouped together. After identification through thresholding, several digital properties of each connected region may then be calculated such as pixel area, orientation, and a coefficient indicating the object circularity. Reference is made to Seo, S. et al, Lensfree holographic imaging for on-chip cytometry and diagnostics, Lab Chip 2009, 9, 777-787 which is incorporated by reference as if set forth fully herein. Thresholded regions of invalid size and shape are discarded and the orientation of the sperm heads is identified as seen in operation 1500. In this operation, a line may be fitted (with respect to orientation and length) to match the major elliptical axis of the head of the sperm 100. In some implementations, the sperm heads may not have an elliptical shape. In this situation, a line may be fitted with respect to a major axis which may have a shape other than elliptical. One condition for a viable sperm is the presence of a healthy tail and therefore for a positive count, the tail must have an adequate length that is also aligned with the orientation of the sperm head. Criteria for healthy sperm tail may be found in World Health Organization (WHO) Laboratory Manual for the Examination of Human Semen and Sperm-Cervical Mucus Interaction; 4th ed.; Cambridge University Press, 1999, which is incorporated by reference herein.

Towards this end, for digital enhancement of the contrast of each sperm tail in the reconstructed phase image, a determinant-of-Hessian filter was applied to extract the ridge-like features of each individual sperm tail. See Su, T. et al., Multi-angle lensless digital holography for depth resolved imaging on a chip, Opt. Express 2010, 18, 9690-9711, which is incorporated herein by reference. A threshold was then applied to the resulting image after which the tails were identified by searching for the remaining ridges in the neighborhood of the endpoints of each sperm head orientation line. Those sperm 100 having tails satisfying the tail length threshold as well as having tails substantially aligned with the orientation of the sperm head were identified as seen in operation 1600. If a ridge is absent from this sperm head neighborhood, or if the tail is not long enough, or has an abnormal shape it was discarded. All the valid sperm were then automatically counted as seen in operation 1700 and marked in the image for further comparison, if necessary.

Figure 4:
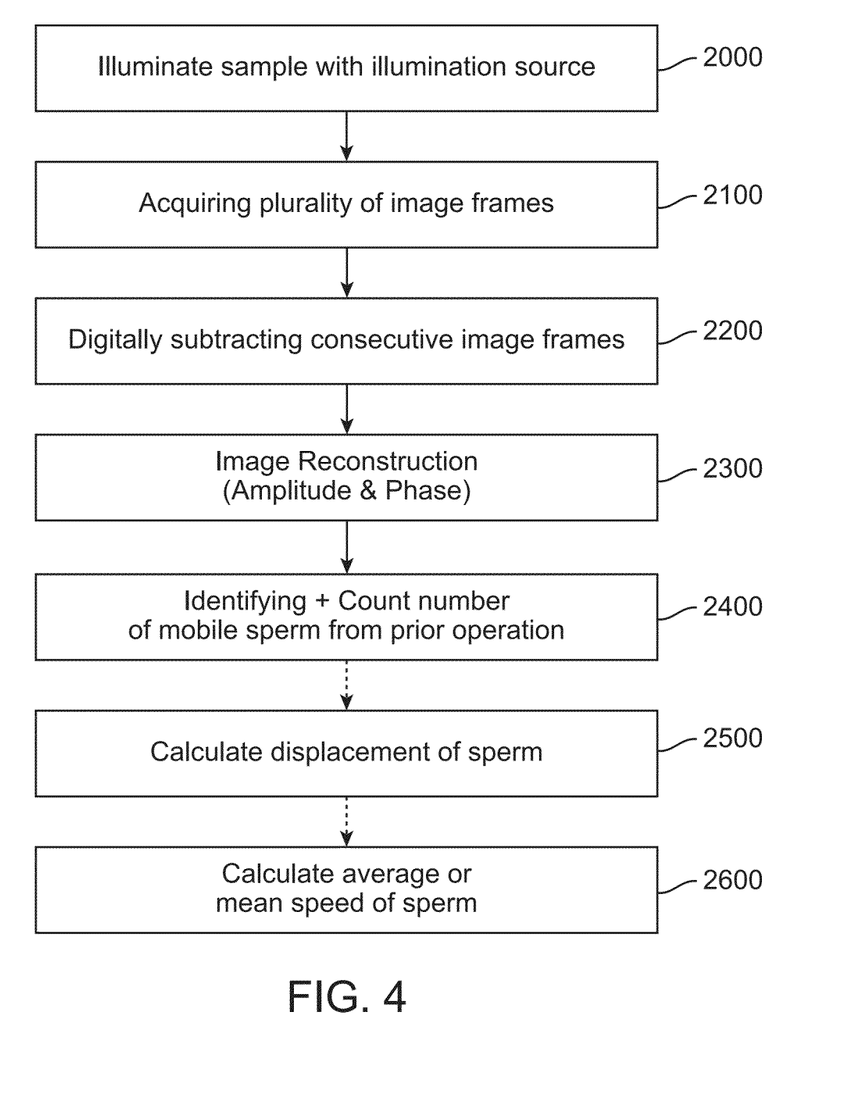
FIG. 4 illustrates a top-level flowchart of how the system automatically analyzes and counts the number of motile sperm cells in a sample.

FIG. 4 illustrates a top-level flowchart of how the system 10 automatically analyzes and counts the number of motile sperm cells 100 in a sample. Motile sperm cells 100 are those sperm cells 100 that that are able to move and thus are able to fertilize eggs. Motile sperm cells 100 are thus important for quantifying and analyzing for the purposes of semen analysis. As seen in operation 2000 of FIG. 4, a sample containing sperm 100 is loaded into the imager 12 and the illumination source 30 is turned on to illuminate the sample. Raw holographic images 38 are then obtained in operation 2100 using the image sensor 36. Next, in operation 2200, consecutive image frames are subtracted from each other to create a new digital hologram that represents differential motion of the sperm 100. The same as operation 1300 in FIG. 3, an iterative algorithm is run (as seen in operation 2300) to create reconstructed holographic images containing amplitude and phase information. In the reconstructed holographic images the motion of each sperm 100 generates one negative (dark) and one positive (bright) spot, which indicate the start and end positions, respectively, of the sperm's motion. These spots may be quantified to provide a count of the number of observed motile sperm as seen in operation 2400. Further, by quantifying the relative distance between these bright and dark spots one can, optionally, simultaneously infer the speed and the trajectories of all the motile sperm within the imaging field-of-view ($\sim 24$ mm$^2$).

For this purpose, the locations of these spots are identified by simple thresholding followed by calculation of their centroid positions. As a result of this, the displacements of individual sperm between consecutive holographic frames can be easily calculated by using the shortest distance between the centroid positions of each dark-bright spot pair. This is illustrated in operation 2500. These displacements of motile sperm in all consecutive frames are linked to each other to plot the dynamic trajectories of the sperm within the FOV. The average or mean speed of each motile sperm can be calculated, as seen in operation 2600, by summing up the magnitudes of its displacements in all frames and dividing this sum with the total duration of the frame acquisition.

Digital processing of the acquired lens-free holographic images, including both immotile sperm detection and motile sperm tracking, may be implemented in software such as Matlab using a processing unit 14 or computer 16. The computation time for each semen sample was $\sim 15$ min for $\sim 24$ mm$^2$ FOV using a PC with an Intel Core2Duo E8400 3.00 GHz CPU. By moving these image processing routines to a GPU (e.g., NVIDIA GeForce GTX 285), the time required to analyze each semen samples can be significantly reduced (by e.g., >10x).

Experimental Results

A self-contained on-chip imaging system 10 was designed and tested to record the holographic images of the semen samples over a field-of-view of $\sim 24$ mm$^2$ with an effective NA of $\sim 0.2$ without utilizing any lenses or scanning mechanical components. This entire lens-free on-chip microscope assembly, which is illustrated in FIG. 2, weighs $\sim 46$ grams and measures $\sim 4.2$ cm$\times 4.2$ cm$\times 5.8$ cm. Inside this on-chip microscope, a simple light-emitting diode (LS E67B, OSRAM Opto Semiconductors, center wavelength: 645 nm, bandwidth: $\sim 15$ nm) is filtered by a 0.1 mm pinhole to provide partially coherent illumination over the semen sample that is placed at a distance of $\sim 4$ cm from the source. Lens-free holograms of the sperm are recorded by a monochrome CMOS image sensor (MT9P031STM, Aptina Imaging, 2.2 $\mu$m pixel size, 5 Megapixel, 24 mm$^2$ active area). This entire imaging system, including the light source and the sensor-chip, is powered and controlled by a laptop computer through a USB 2.0 connection. A smart-phone or a personal digital assistant (PDA) could also be used for the same purpose. The sample of interest is loaded into this microscope using a sliding sample tray and held at $\sim 1$ mm above the active area of the CMOS image sensor.

Frozen semen specimens were obtained from California Cyrobank and were stored in liquid nitrogen. Before use, the specimen vials were thawed in 37° C. water bath for 10 minutes to revive the sperm. A sperm washing medium (9983, Irvine Scientific), pre-mixed with a small number of 20 $\mu$m polystyrene microspheres (4220A, Thermo Scientific, $\sim 40$ beads/$\mu$L), was used to dilute the semen sample to a desired concentration. The diluted semen was pipetted into a glass sperm counting chamber (DRM-600, Millennium Sciences, chamber depth: 20 $\mu$m) and then enclosed with a No. 1 glass cover slip (12-548A, Fisher Scientific) to suppress liquid evaporation. The added microspheres act as mechanical spacers to ensure a constant chamber height and a uniform sperm distribution. For preparing semen samples with immobilized sperm, the diluent was replaced by a bicarbonate-formalin diluting fluid (6710-4, Ricca Chemical) while the rest of the procedures remained the same.

Figure 5A:
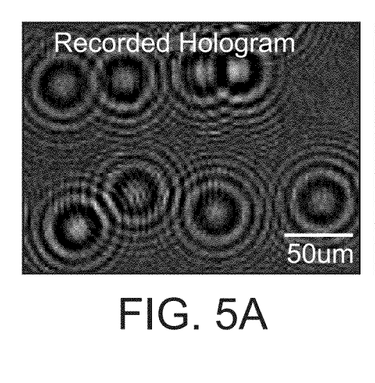
FIG. 5A illustrates a digitally cropped lens-free hologram of an immobilized semen sample (6.05 million sperm per mL) that is acquired with the unit in FIG. 2.
Figure 5B:
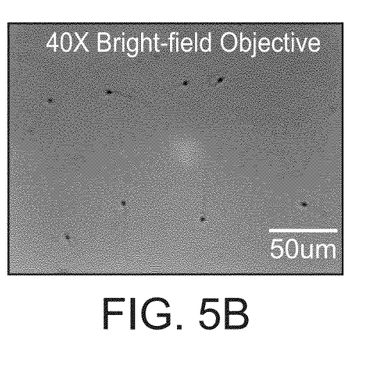
FIG. 5B illustrates a bright-field microscope image of the same FOV as in FIG. 5A with a 40× objective lens (NA=0.65).

Consecutive lens-free holographic frames (20) for each semen sample of interest were recorded using the on-chip imager shown in FIG. 2 at a frame rate of 2 frames per second (FPS) and an integration time of $\sim 35$ milliseconds per frame. FIG. 5A illustrates a digitally cropped lens-free hologram of an immobilized semen sample (6.05 million sperm per mL) that is acquired with the unit in FIG. 2. FIG. 5B illustrates a bright-field microscope image of the same FOV as in FIG. 5A with a 40x objective lens (NA=0.65). Two different processing approaches, digital summation and subtraction of these lens-free holographic frames, were applied to separately identify and quantify the immotile and the motile sperm in the semen sample as described herein.

For identification and quantification of the immotile sperm, all the individual holographic images were normalized to their own mean intensity and then were summed up digitally. This summation operation not only increases the digital signal-to-noise ratio (SNR) of the immotile sperms' holograms, but also smears out the lens-free holograms of the motile sperm. As a result, this step creates sufficient contrast and SNR to observe the faint images of the sperms' tails, which enables automated identification of their signatures from the background.

Figure 5C:
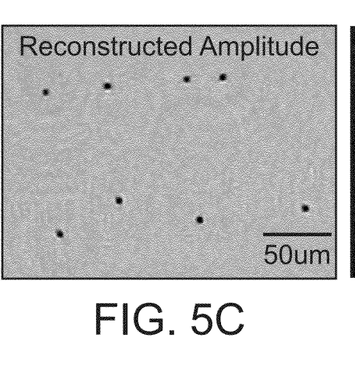
FIG. 5C illustrates the amplitude image reconstructed from the raw hologram shown in FIG. 5A for the same FOV indicates the locations of the heads of the sperm.
Figure 5D:
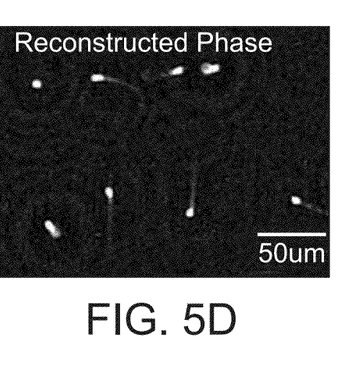
FIG. 5D illustrates the phase image reconstructed from the raw hologram shown in FIG. 5A for the same FOV illustrates both the heads and the tails of the sperm.

An iterative holographic reconstruction algorithm as explained herein was used to process the summation hologram and reconstruct the microscopic images of the immotile sperm. FIG. 5C illustrates the amplitude image reconstructed from the raw hologram shown in FIG. 5A for the same FOV indicates the locations of the heads of the sperm. FIG. 5D illustrates the phase image reconstructed from the raw hologram shown in FIG. 5A for the same FOV illustrates both the heads and the tails of the sperm. An interesting observation based on these images is that the sperm tails can only be observed in the reconstructed phase images, while the heads of the sperm are clearly visible in both the amplitude and the phase images. The main reason behind this behavior is that the tail of a sperm is a sub-micron structure which generates a rather weak scattering signal. Therefore, with the limited NA and SNR of the wide-field lens-free microscope, such a small feature does not contribute enough scattering signal to be reconstructed in the amplitude image. On the other hand, the refractive index difference between the tail and the surrounding medium still creates a sufficient contrast in the reconstructed phase image, permitting observation and automated detection of the sperm tails.

For automated counting of immotile sperm, candidate objects were initially screened by their distinct and bright elliptical heads in the reconstructed phase images as seen in FIG. 5D. These immotile sperm candidates were isolated from the background through a threshold operation, where pixels above a certain intensity value were grouped together. After this thresholding step, several digital properties of each connected region were calculated such as its pixel area, orientation, and a coefficient indicating the object circularity.

Figure 6A:
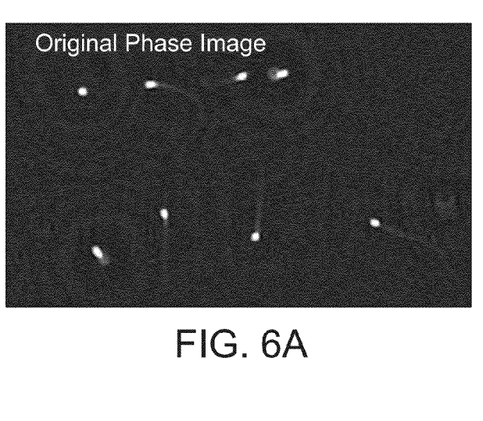
FIG. 6A illustrates a reconstructed phase image containing eight (8) sperm with different morphologies and orientations (same sample and FOV as in FIG. 5D).
Figure 6B:
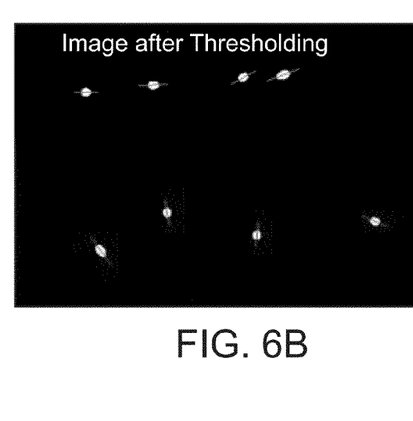
FIG. 6B illustrates a new image that was digitally generated by thresholding the intensity of the image shown in FIG. 6A to highlight the position and the orientation of each sperm head. The lines passing through the bright spots (sperm heads) indicate the orientations (i.e., the major axis) of the elliptical sperm heads.

Thresholded regions of invalid size or shape were discarded, and a line was fitted to match the orientation and the length of the fitted ellipse to each sperm head. FIG. 6A illustrates a reconstructed phase image containing eight (8) sperm with different morpohologies and orientations (same sample and FOV as in FIG. 5D). FIG. 6B illustrates a new image that was digitally generated by thresholding the intensity of the image shown in FIG. 6A to highlight the position and the orientation of each sperm head. The lines passing through the bright spots (sperm heads) indicate the orientations (i.e., the major axis) of the elliptical sperm heads.

Figure 6C:
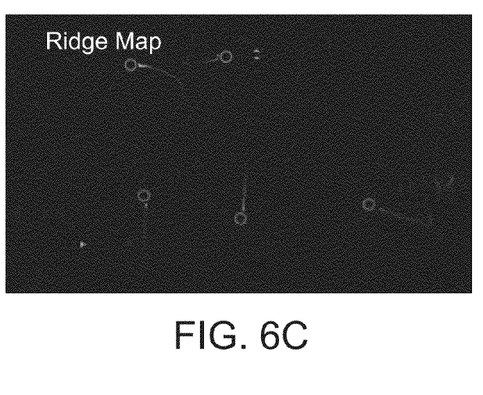
FIG. 6C illustrates a ridge map of the original phase image shown in FIG. 6A that was generated using a determinant-of-Hessian filter. Positions of the sperm heads in this image are marked with circles.

Following this initial screening step, the tail of each sperm must also be identified and matched to its corresponding sperm head orientation. In order to have a viable sperm and therefore a for a positive count, there needs to be the presence of a healthy tail with an adequate length that is also aligned with the orientation of the sperm head. Towards this end, for digital enhancement of the contrast of each tail in the reconstructed phase image, a determinant-of-Hessian filter was applied to extract the ridge-like features of each individual sperm tail. FIG. 6C illustrates a ridge map of the original phase image shown in FIG. 6A that was generated using a determinant-of-Hessian filter. Positions of the sperm heads in this image are marked with circles.

Figure 5E:
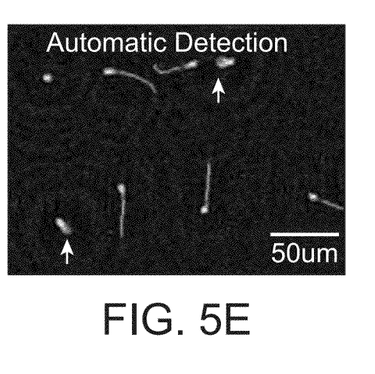
FIG. 5E illustrates the automatic characterization results that are generated based on the reconstructed phase image in FIG. 5D.
Figure 6D:
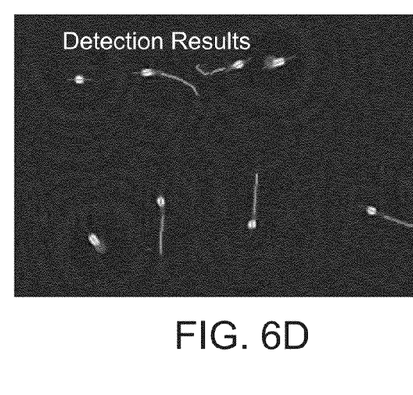
FIG. 6D illustrates the automatic detection of viable sperm cells by matching the tail lines and head lines.

A threshold was then applied to the resulting image after which the tails were identified by searching for the remaining ridges in the neighborhood of the endpoints of each head orientation line. FIG. 6D illustrates the automatic detection of viable sperm cells by matching the tail lines and head lines. FIG. 5E illustrates the automatic characterization results that are generated based on the reconstructed phase image in FIG. 5D. The elliptical areas corresponding to sperm heads are enclosed by circles while the tails are labeled with lines. Defective sperm with missing or unusually curved tails (marked with the white arrows in FIG. 5E) are not reported towards positive sperm counts. If a ridge is absent from this sperm head neighborhood, or if the tail is not long enough, or has an abnormal shape it was discarded. All the valid sperm were then automatically counted and marked in the image for further comparison, if necessary.

Figure 7A:
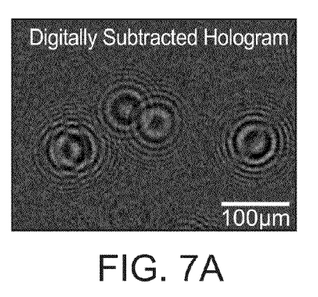
FIG. 7A illustrates a digitally subtracted lens-free hologram of three moving sperm generated from two successive frames (500 milliseconds apart).
Figure 7B:
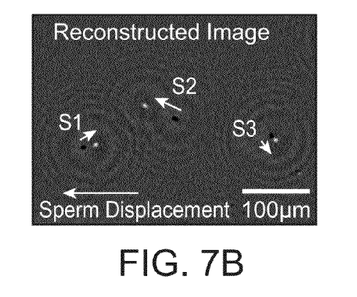
FIG. 7B illustrates a digitally reconstructed image of FIG. 7A showing the differential motion of the motile sperm. In the reconstructed holographic images, the motion of each sperm generates one negative (dark) and one positive (bright) spot, which indicate the start and the end positions of the sperm's motion, respectively. The displacement vectors of these sperm are labeled as S1, S2, and S3.

Quantification of the motile sperm in semen is a relatively easier task for the system since the only moving objects within the sample are the motile sperm. For this purpose, consecutive lens-free holographic frames were digitally subtracted from each other to create new digital holograms that represent differential motion of the sperm. FIG. 7A illustrates a digitally subtracted lens-free hologram of three moving sperm is generated from two successive frames (500 milliseconds apart). The same iterative algorithm discussed above was then used to reconstruct the differential motion of the motile sperm as shown in FIG. 7B. In these reconstructed holographic images, the motion of each sperm generates one negative (dark) and one positive (bright) spot, which indicate the start and the end positions of the sperm's motion, respectively.

By quantifying the relative distance between these bright and dark spots one can simultaneously infer the speed and the trajectories of all the motile sperm within the imaging field-of-view (~24 mm$^2$). For this purpose, the locations of these spots were identified by simple thresholding followed by calculation of their centroid positions. See Su, T. et al., Multi-angle lensless digital holography for depth resolved imaging on a chip, Opt. Express 2010, 18, 9690-9711. As a result of this, the displacements of individual sperm between consecutive holographic frames can be calculated by using the shortest distance between the centroid positions of each dark-bright spot pair (FIG. 7B). FIG. 7B illustrates the positions of three sperm in two successive frames (white spots show the sperm's respective end positions and black spots show their starting positions. The displacement vectors of these sperm cells are labeled as S1, S2, and S3

Figure 8A:
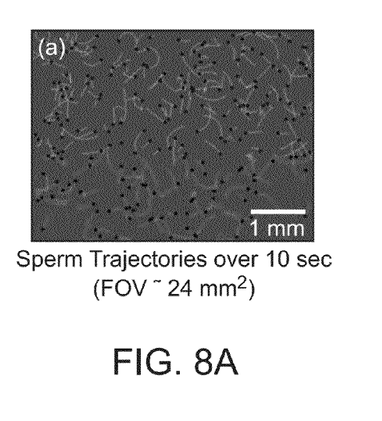
FIG. 8A illustrates dynamic trajectories of 221 sperm within a field-of-view of ~24 mm$^2$ that are automatically tracked over a time-span of 10 seconds.
Figure 8B:
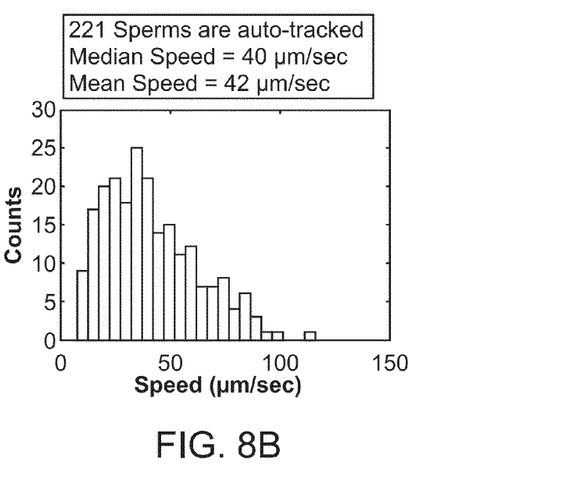
FIG. 8B illustrates a histogram of sperm speed for the 221 sperm of FIG. 8A.

The displacements of the motile sperm in all consecutive frames are then linked to each other to plot the dynamic trajectories of the sperm within the FOV. FIG. 8A illustrates dynamic trajectories of 221 sperm within a field-of-view of ~24 mm$^2$ that are automatically tracked over a time-span of 10 seconds. The spots mark the end positions of the tracked sperm cells, while the green lines refer to their respective trajectories. The average speed of each motile sperm was calculated by summing up the magnitudes of its displacements in all frames and dividing this sum with the total duration of the frame acquisition. FIG. 8B illustrates a histogram of sperm speed for the 221 sperm of FIG. 8A.

Digital processing of the acquired lens-free holographic images, including both immotile sperm detection and motile sperm tracking, were implemented in Matlab. The computation time for each semen sample was ~15 min for ~24 mm$^2$ FOV using a PC with an Intel Core2Duo E8400 3.00 GHz CPU. By moving these image processing routines to a GPU (e.g., NVIDIA GeForce GTX 285), the time required to analyze each semen samples can be significantly reduced (by e.g., >10×).

To verify the automatic characterization results made with the holographic on-chip imaging system, videos of the same semen samples were also recorded using a conventional bright-field microscope (ME300TZ-2L-5M, AmScope). For each semen sample, the videos were recorded across≥9 adjacent FOVs (~0.20 mm$^2$ each) using a 20× objective-lens (NT38-339, Edmund Optics, NA=0.4). Motile and immotile sperm were then separately counted on the recorded video by visual inspection, following the WHO guidelines. For samples that had less than 0.5 million motile sperm per mL, videos were also recorded with a 10× objective-lens (NA=0.25) that had a relatively larger field-of-view than a 20× objective-lens. However, these lower resolution videos were used for counting of motile sperm only, and were not used to quantify immotile sperm densities.

Figure 9A:
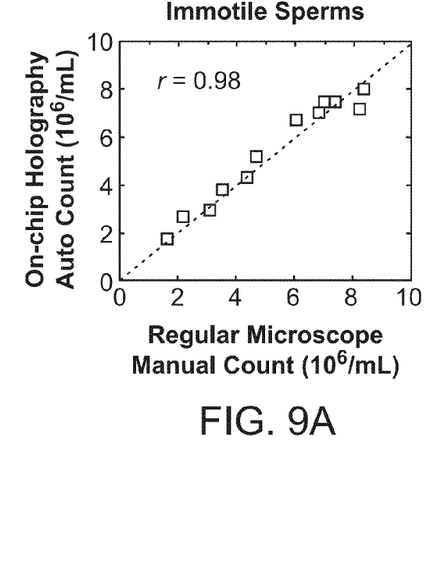
FIG. 9A compares the counting accuracy of the automated semen analysis platform for immotile sperm with regular microscope counting.
Figure 9B:
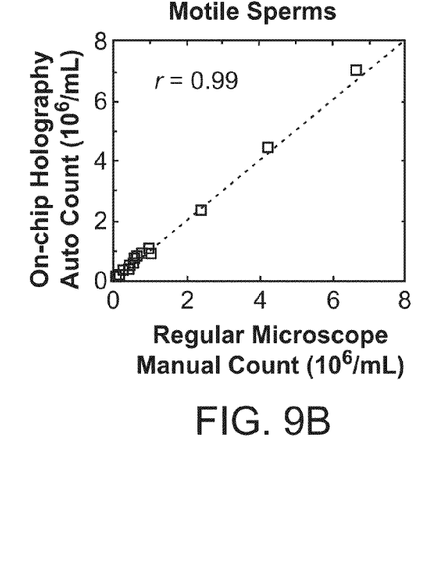
FIG. 9B compares the counting accuracy of the automated semen analysis platform for motile sperm with regular microscope counting.
Figure 9C:
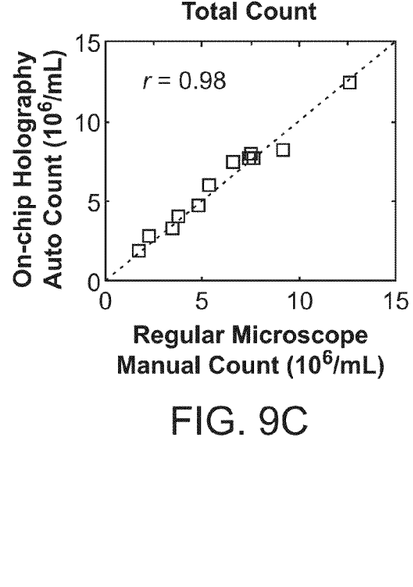
FIG. 9C illustrates the total counts of both immotile and motile sperm.

Twelve (12) semen samples containing both immotile and motile sperm at varying concentrations were tested to validate the automated counting accuracy of the system. FIG. 9A compares the counting accuracy of the automated semen analysis platform for immotile sperm with regular microscope counting. FIG. 9B compares the counting accuracy of the automated semen analysis platform for motile sperm with regular microscope counting. FIG. 9C illustrates the total counts of both immotile and motile sperm. The x-axes are the sperm concentrations that are manually counted using a conventional bright-field microscope. The y-axes are the sperm concentrations that are automatically counted for the same semen samples using lens-free holographic images acquired with the on-chip microscope shown in FIG. 2. Correlation coefficients (r) of these characterization results shown in FIGS. 9A, 9B, and 9C (0.98, 0.99, and 0.98, respectively) further validate the accuracy of this compact and light-weight holographic lens-free microscope as a semen analysis platform.

Still referring to FIGS. 9A-9C, the comparison confirms that the automated analysis can accurately quantify the concentration of both immotile and motile sperm up to a density of 8.3 and 6.8 Million/mL, respectively. Such a large dynamic range allowed the system to reliably analyze human semen samples that were diluted by ~1-10×. In addition to this, FIGS. 9A-9C also reveal the automated platform's superior ability to analyze semen samples with very low sperm concentrations. For example, the lowest concentration reported in FIG. 9B, 87,500 sperm/mL, corresponds to ~42 sperm tracked by the system over its 24 mm$^2$ field-of-view. To achieve the same level of statistical characterization accuracy for such a low density semen sample, a conventional microscope equipped with a 20× objective-lens would need to look at close to 100 different field-of-views, making it quite inconvenient. Therefore, the large field-of-view of the lens-free on-chip imaging platform is also quite valuable for providing quantitative results at extremely low sperm densities such as observed in post-vasectomy.

While embodiments have been shown and described, various modifications may be made without departing from the scope of the inventive concepts disclosed herein. The invention(s), therefore, should not be limited, except to the following claims, and their equivalents.

What is claimed is:

1. A system for the automated analysis of sperm comprising:
    an imager comprising a sample holder configured to receive a sample containing sperm and an illumination source configured to illuminate a first side of the sample holder through a spatial filter interposed between the illumination source and the sample holder;
    an image sensor disposed on a second, opposite side of the sample holder configured to acquire a plurality of image frames of the sperm in the sample, the plurality of image frames containing holographic images of the sperm; and
    a computing device including a processing unit operably coupled to the image sensor and executing a software program thereon, the software selectable to perform at least one of: (i) automatically sum the plurality of image frames and identify the immotile sperm based at least in part on the on the automatic summation, and (ii) automatically subtract consecutive image frames of the plurality of image frames and identify the motile sperm based at least in part on the automatic subtraction.

2. The system of claim 1, wherein the summation produces a summation hologram and the software is configured to reconstruct the summation hologram into image frames containing amplitude and phase information.

3. The system of claim 2, wherein the software is configured to isolate sperm heads in the image frames containing phase information.

4. The system of claim 3, wherein the software is configured to identify the orientation of each sperm head.

5. The system of claim 4, wherein the software is configured to identify sperm tails having a tail length above a threshold value and a tail orientation aligned with the orientation of each sperm head.

6. The system of claim 5, wherein the software is configured to count the number of immotile sperm based on the total number of sperm having a tail length above a threshold value and a tail orientation aligned with the orientation of each sperm head.

7. The system of claim 1, wherein the software is configured to reconstruct an image obtained from the subtracted image frames into an image containing amplitude and phase information of the motile sperm.

8. The system of claim 7, wherein the software is configured to calculate displacement of a plurality of sperm based on the image containing amplitude and phase information.

9. The system of claim 8, wherein the software is configured to calculate the average speed of the plurality of sperm over their respective displacements.

10. The system of claim 9, wherein the software is configured to calculate statistical speed histograms of the plurality of sperms.

11. A method of automatically analyzing immotile sperm comprising:
    illuminating a first side of a sample holder configured to receive a sample containing sperm with an illumination source emitting at least partially coherent light, the at least partially coherent light passing through an aperture prior to illuminating the sample holder;
    acquiring a plurality of image frames of the sample with an image sensor disposed on an opposing side of the sample holder;
    creating a summation hologram based on a digital summation of the plurality of image frames;
    reconstructing the summation hologram into reconstructed frame images containing amplitude and phase information;
    isolating sperm heads in the reconstructed frame image containing phase information;
    identify the orientation of each sperm head;
    identify sperm tails having a tail length above a threshold value and a tail orientation aligned with the orientation of each sperm head; and
    counting the number of immotile sperm based on the total number of sperm having a tail length above a threshold value and a tail orientation aligned with the orientation of each sperm head.

12. The method of claim 11, wherein isolating sperm heads comprises identifying bright shapes in the reconstructed phase image.

13. The method of claim 11, wherein isolating sperm heads further comprises eliminating thresholded regions of invalid size or shape.

14. The method of claim 11, wherein identifying the orientation of each sperm head comprises line fitting the major axis of each sperm head.

15. The method of claim 11, wherein identifying the sperm tails comprises increasing the contrast of the reconstructed phase image and matching, for each sperm head, visible tails having a tail length above a threshold value and a tail orientation aligned with the orientation of a corresponding sperm head.

16. A method of automatically analyzing sperm comprising:
illuminating a first side of a sample holder configured to receive a sample containing sperm with an illumination source emitting at least partially coherent light, the at least partially coherent light passing through an aperture prior to illuminating the sample holder;
acquiring a plurality of image frames of the sample with an image sensor disposed on an opposing side of the sample holder;
digitally summing the plurality of image frames and identifying immotile sperm based at least in part on the digital summation;
digitally subtracting consecutive image frames and produce an image representative of motion of the sperm;
identifying motile sperm in the image representative of motion of the sperm and counting the number of mobile sperm; and
identifying immotile sperm in the digitally summed image and counting the number of immotile sperm.

17. The method of claim 16, wherein the image representative of motion of the sperm is reconstructed into at least one of a reconstructed phase image and a reconstructed amplitude image.

18. The method of claim 17, further comprising calculating the displacement of the motile sperm based on the reconstructed phase image or the reconstructed amplitude image.

19. The method of claim 18, further comprising calculating the average speed of the motile sperm over the displacement.

20. The method of claim 19, further comprising calculating the statistical speed histograms of the motile sperm.

* * * * *